US012622612B2

(12) United States Patent
Graversen et al.

(10) Patent No.: US 12,622,612 B2
(45) Date of Patent: May 12, 2026

(54) METHOD FOR PROVIDING DECISION SUPPORT IN RELATION TO A PATIENT RECEIVING OXYGEN TREATMENT

(71) Applicant: Obi ApS, Hadsund (DK)

(72) Inventors: Bruno Graversen, Hadsund (DK); Bjarne Flou, Hadsund (DK)

(73) Assignee: Roche Diagnostics A/S, Copenhaven V (DK)

( * ) Notice: Subject to any disclaimer, the term of this patent is extended or adjusted under 35 U.S.C. 154(b) by 1150 days.

(21) Appl. No.: 17/430,959

(22) PCT Filed: Feb. 26, 2020

(86) PCT No.: PCT/EP2020/055046
§ 371 (c)(1),
(2) Date: Aug. 13, 2021

(87) PCT Pub. No.: WO2020/174013
PCT Pub. Date: Sep. 3, 2020

(65) Prior Publication Data
US 2022/0142528 A1     May 12, 2022

(30) Foreign Application Priority Data

Feb. 26, 2019    (EP) .................................... 19159480

(51) Int. Cl.
*A61B 5/1455*     (2006.01)
*A61M 16/00*     (2006.01)
(Continued)

(52) U.S. Cl.
CPC ..... *A61B 5/14551* (2013.01); *A61M 16/0003* (2014.02); *A61M 16/026* (2017.08);
(Continued)

(58) Field of Classification Search
CPC .......... A61B 5/14551; A61M 16/0003; A61M 16/101; A61M 16/026; A61M 2016/1025;
(Continued)

(56) References Cited

U.S. PATENT DOCUMENTS 5,922,607 A     7/1999 Bernreuter
6,042,550 A *   3/2000 Haryadi ............... A61B 5/0836
                                                   600/483
(Continued)

FOREIGN PATENT DOCUMENTS

JP     2002301154 A   10/2002
WO    2004010861 A2    2/2004
(Continued)

OTHER PUBLICATIONS

Tygesen, et al., "Mathemtaical arterialization of venous blood in emergency medicine patients", Lippincott Williams & Wilkins, vol. 00, No. 00, pp. 1-10, 2011.
(Continued)

*Primary Examiner* — Alex M Valvis
*Assistant Examiner* — Jonathan M Haney
(74) *Attorney, Agent, or Firm* — Thomas E. Lees, LLC

(57) ABSTRACT

The invention relates to a computer implemented method, and a data processing system, for providing decision support in relation to a patient receiving oxygen treatment, the patient having a medical condition requiring a supplemental oxygen device providing an oxygen flow, wherein the decision support assists a health care person in adjusting the oxygen flow from said supplemental oxygen device to the patient, and wherein the decision support uses an arterial oxygenation value to calculate whether the oxygen flow to the patient is sufficient based on a desired input from the health care person.

5 Claims, 9 Drawing Sheets

(51) Int. Cl.

| | |
|---|---|
| *A61M 16/10* | (2006.01) |
| *G16H 20/40* | (2018.01) |
| *G16H 40/20* | (2018.01) |
| *G16H 40/63* | (2018.01) |
| *G16H 50/20* | (2018.01) |
| *G16H 50/50* | (2018.01) |

(52) U.S. Cl.

CPC .......... *A61M 16/101* (2014.02); *G16H 20/40* (2018.01); *G16H 40/20* (2018.01); *G16H 40/63* (2018.01); *G16H 50/20* (2018.01); *G16H 50/50* (2018.01); *A61M 2016/1025* (2013.01); *A61M 2230/205* (2013.01)

(58) Field of Classification Search

CPC . A61M 2230/205; G16H 20/40; G16H 40/20; G16H 40/63; G16H 50/50; G16H 50/20
See application file for complete search history.

(56) References Cited

U.S. PATENT DOCUMENTS

| | | | |
|---|---|---|---|
| 2002/0017299 A1* | 2/2002 | Hickle ................. | A61B 5/4821 |
| | | | 128/205.25 |
| 2006/0105319 A1 | 5/2006 | Rees et al. | |
| 2006/0185669 A1* | 8/2006 | Bassovitch ....... | A61M 16/0045 |
| | | | 128/205.26 |
| 2006/0257283 A1* | 11/2006 | Ranucci ................. | A61B 5/082 |
| | | | 422/45 |
| 2007/0218559 A1 | 9/2007 | Franco | |
| 2011/0041850 A1* | 2/2011 | Vandine ............ | A61M 16/0069 |
| | | | 128/204.23 |
| 2011/0290252 A1* | 12/2011 | Amjad ................ | A61M 16/026 |
| | | | 128/204.23 |
| 2012/0065482 A1 | 3/2012 | Robinson et al. | |
| 2013/0345572 A1 | 12/2013 | Karbing et al. | |
| 2014/0275901 A1* | 9/2014 | Flanagan ............. | A61B 5/7275 |
| | | | 600/364 |
| 2016/0000989 A1* | 1/2016 | Haag ................... | A61M 1/3627 |
| 2017/0255756 A1* | 9/2017 | Karbing .............. | A61M 16/026 |
| 2018/0099109 A1 | 4/2018 | Kinsky et al. | |

FOREIGN PATENT DOCUMENTS

| | | | |
|---|---|---|---|
| WO | 2014049484 A1 | 4/2014 |
| WO | 2016142657 A1 | 9/2016 |

OTHER PUBLICATIONS

Toftegaard, "A mathematical model based method for converting venous values of acid-based and oxygenation status of arterial values", Aalborg Universiteit, 2010.

Rees, et al., "Calculating acid-base and oxygenation status during COPD exacerbation using mathematically arterialised venous blood", Aalborg University, pp. 1-8, 2012.

Rees, et al., "Converting venous acid-based and oxygen status to arterial in patients with lung disease", European Respiratory Journal, vol. 22, No. 5, pp. 1141-1147, 2009.

Toftegaard et al., "Evaluation of a method for converting venous valves of acid-base and oxygenation status to arterial values", Emerg Med J, vol. 26, pp. 268-272, 2009.

Magnet, et al., "Capillary $PO_2$ does not adequately reflect arterial $PO_2$ in hypoxemic COPD patients", International Journal of COPD, vol. 12, pp. 2647-2653, 2017.

Rees, et al., "A method for calculation of arterial acid-base and blood gas status from measurements in the peripheral venous blood", Computer Methods and Programs in Biomedicine, vol. 81, pp. 18-25, 2006.

Rees, et al., "Mathematical modelling of the acid-base chemistry and oxygenation of blood: a mass balance, mass action approach including plasma and red blood cells", Eur. J. Appl. Physiol, vol. 108, pp. 483-494, 2010.

Rees, "The Intelligent Ventilator (Invent) project: The role of mathematical models in translating physiological knowledge into clinical practice", Computer Methods and Programs in Biomedicine, pp. S1-S29, 2011.

International Search Report in reference to co-pending European Patent Application No. PCT/EP2020/055046 filed Feb. 26, 2020.

Written Opinion in reference to co-pending European Patent Application No. PCT/EP2020/055046 filed Feb. 26, 2020.

Jeong et al., Availability of Capillary Blood Gas Analysis in Neonate, Journal of Korean Pediatric Society, Sepsis 4:17 (2002).

Korean first Office action for Korean Patent Application No. 10-2021-7030344; Korean Intellectual Property Office; Patent Office; Republic of Korea; dated Jun. 19, 2024.

\* cited by examiner

| | CBG for all | CBG with target | VBG+v-TAC for baseline CBG+v-TAC for final | VBG+v-TAC for baseline VBG+v-TAC for final |
|---|---|---|---|---|
| Baseline | Baseline 20 min | Baseline 20 min | Baseline 15 min | Baseline 15 min |
| Adjust | Adjust (n)*20min | Adjust (n)*10min+10min | Adjust (n)*10min+10min | Adjust (n)*10min+5min |
| Review | Review | Review | Review | Review |
| n | CBG, for all | CBG with target | VBG + CBG | VBG + VBG |
| 0 (0%) | 20 (0min) | 20 (0min) | 20 (0min) | 15 (0min) |
| 1 (60%) | 40 (24 min) | 40 (24min) | 35 (21min) | 30 (18min) |
| 2 (20%) | 60 (12 min) | 50 (10min) | 45 (9min) | 40 (8min) |
| 3 (20%) | 80 (16 min) | 60 (12min) | 55 (11min) | 50 (10min) |
| 4 (0%) | 100 (0 min) | 70 (0min) | 65 (0min) | 60 (0min) |
| | 52 min // Baseline | 46 min // ~11,5% | 41 min // ~21,2% | 36 min // ~30,8% |

Fig. 7

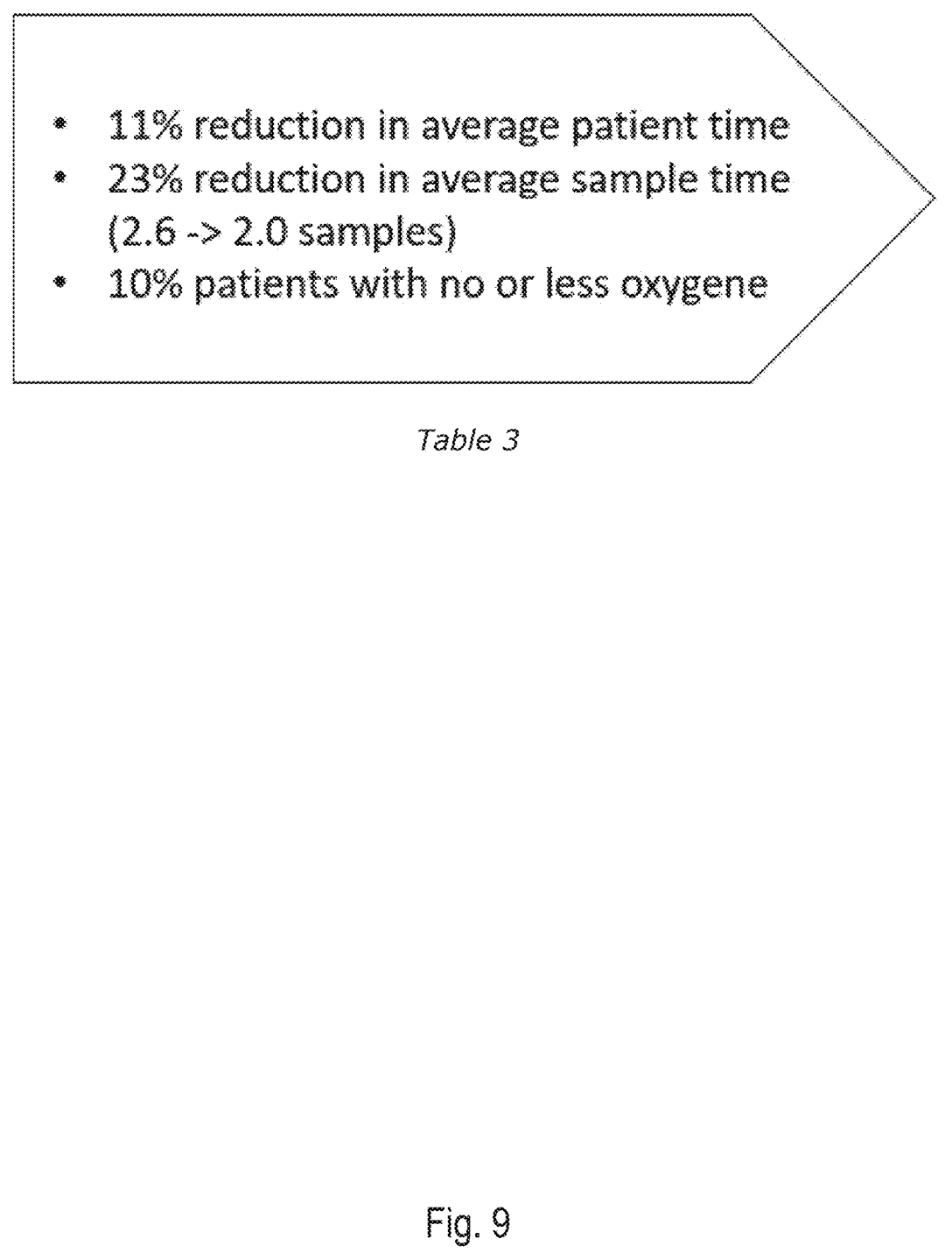

- 11% reduction in average patient time
- 23% reduction in average sample time (2.6 -> 2.0 samples)
- 10% patients with no or less oxygene

*Table 3*

Fig. 9

METHOD FOR PROVIDING DECISION SUPPORT IN RELATION TO A PATIENT RECEIVING OXYGEN TREATMENT

FIELD OF THE INVENTION

The present invention relates to a method of providing decision support and a data processing system in relation to a patient receiving oxygen treatment (OT) or long-term oxygen treatment (LTOT), said patient having a medical condition, such as COPD, requiring a supplemental oxygen device for providing an oxygen flow, typically on a continuous or permanent way. The decision support assists a health care person, such as a nurse, in titrating the oxygen flow from said supplemental oxygen device to the patient. The invention also relates to a corresponding decision support system (DSS), preferably a portable data processing system, and a corresponding computer program product.

BACKGROUND OF THE INVENTION

A proportion of patients with respiratory problems (e.g. COPD) are receiving treatment where a target pO2 is of interest. An example is LTOT (Long Term Oxygen Therapy) which in some cases are delivered at home. Titration of LTOT is handled different from country to country using arterial blood gas, capillary blood gas etc. As an example, the guidelines from UK is using arterial blood gas and describes that use of capillary blood gas will result in patients receiving LTOT without need. In Germany where capillary blood gas (CBG) is more commonly used studies find that 20-30% of the patients receive LTOT without a clinical need when using capillary blood gas, see *Kapillärer PO2 reflektiert nicht adäquat den arteriellen PO2 bei hypoxämischen COPD-Patienten*; Magnet F S et. al.; *Int J COPD* 2017; 12:2647-2653. The Danish guideline is based on arterial blood gas with a baseline and one sample per litre oxygen increase. This method will also allow for optimization of oxygen titration for patients following any of these guidelines.

Complexity, patient pain and resource constraints is driving hospital towards more patient-friendly methods which at the same time can be delivered by a wider pool of resources e.g. CBG (capillary blood gas) with the limitation this method has.

Current methods are based on guidelines using arterial blood gas. A baseline sample is typically drawn and oxygen flow is increased in steps of 1 litre/minute. After a set period, e.g. 30 minutes, another sample is drawn and if paO2 is below a set threshold, e.g. 8 kPa/60 mmHg, the process is repeated until the threshold is achieved. Due to resource constraints clinical practice is often different and capillary blood gas is used as alternative.

Based on input from Germany, a process when titrating oxygen using CBG is as follows:

1. Oxygen is removed
2. Baseline CBG (including vasodilation crème applied 10 minutes before sampling)
3. Adjust+1|O2
4. New CBG
5. Compare with target pO2 (e.g. 65 mmHg)
6. If target achieved continue—if not jump to step 3
7. Subscribe achieved oxygen flow rate to patient.

This current method implies a baseline CBG and a review CBG for each step of oxygen (0 litre/min=1 sample; 1 litre/min=2 samples etc.). Review of 10 patients resulted in 26 samples in total (2.6 per patient), however this group had 3 litre/min as the highest flow-rate. Feedback from clinics indicates that some patients have up to 7-8 samples drawn during titration, which could indicate that the average number of samples would be higher.

Even though best practice is based on ABG and most guidelines recommends ABG over alternatives, CBG increasingly being used due to resource constraints and increasing number of patients.

There is a need for continuous innovation in the healthcare system due to an increasing number of patients requiring support from a healthcare system, which cannot expand with the same rate. Patients receiving too much oxygen is at risk of harm. E.g. COPD patients are risking hypercapnia and acidosis. Even worse is some patients receiving home oxygen without a clinical need, since receiving home oxygen is costly and impacts the patient's social life.

Hence, an improved method for providing decision support in relation to a patient receiving oxygen treatment (OT), preferably long-term oxygen treatment (LTOT), would be advantageous, and in particular a more efficient and/or reliable method would be advantageous.

OBJECT OF THE INVENTION

It is a further object of the present invention to provide an alternative to the prior art.

In particular, it may be seen as an object of the present invention to provide a decision support in relation to a patient receiving oxygen treatment (OT), that solves the above-mentioned problems of the prior art with a complex, unnecessary and/or unsafe adjustment of the supplemental oxygen flow for the patient.

SUMMARY OF THE INVENTION

Thus, the above described object and several other objects are intended to be obtained in a first aspect of the invention by providing a computer implemented method for providing decision support in relation to a patient receiving oxygen treatment, said patient having a medical condition requiring a supplemental oxygen device providing an oxygen flow, wherein the decision support assists a health care person in adjusting the oxygen flow from said supplemental oxygen device to the patient, the method comprising:

providing blood gas values in a blood sample from the patient to determine a baseline, providing an arterial oxygenation value of the patient, if said blood gas values are not derived from an arterial blood sample, calculating a relationship between an oxygen level of the patient and the arterial oxygenation value of the patient by applying a mathematical model to the measured arterial oxygenation value and measured blood gas values and projection of the oxygen level from said baseline, calculating a target arterial oxygenation value representing a desired target oxygen level (target_pO2) of the patient based on said calculated relationship and projection between the oxygen level of the patient and the arterial oxygenation value of the patient, providing decision support for adjusting the oxygen flow from the supplemental oxygen device to the patient based on the measured arterial oxygen value of the patient, until the target arterial oxygenation level is reached, and optionally providing the blood gas value in a blood sample from the patient to confirm the desired target oxygen level of the patient is reached.

The invention is particularly, but not exclusively, advantageous for obtaining decision support when adjusting oxygen flow to a patient from a supplementary oxygen device. The decision support can assist health care personnel, such as a nurse or physician to, with fewer than usual adjustments of the oxygen flow, reach a desired oxygen level of the patient. The fewer than usual adjustments saves time for the health care personnel and furthermore reduces the amount of time at which the patient is in discomfort.

Another advantage of the present invention is the reduced amount of blood samples, which is needed from a patient to adjust the oxygen flow. Especially arterial blood samples are associated with risk of side effects and discomfort to the patient. The present invention enables a health care person to beside arterial blood, to use a capillary or venous blood sample, which are less uncomfortable, than an arterial blood sample. Furthermore, less blood samples are required, as the present invention, in most cases, only needs to establish a blood gas base line, which in turn requires one blood sample. Currently, guide-lines require that a confirmatory blood sample is analysed to ensure correct oxygen levels within the patient but the present invention has, so far, proved to be reliable, therefore the present invention might obsolete current practice in relation to said confirmatory blood sample, hence reduce the required amount of blood samples from a patient, to one sample.

The reduced adjustment time has a secondary advantage, in that more time to adjust the oxygen flow can lower the oxygen flow increments from e.g. 1 L/min to 0.5 or 0.2 L/min so as to more accurately adjust the oxygen flow to the patient, reducing the amount of oxygen supplied to the patient on long-term basis.

It is to be understood, that an advantage of the present invention, is, that in many cases, only a single blood sample is required to provide decision support for the adjustment of the oxygen flow and only a second blood sample is to be used for confirmation of correct adjustment of the set oxygen flow for the patient.

In the context of the present invention, oxygen flow is to be understood as the amount of oxygen flowing to a patients airways, from an oxygen source, measured in litres supplied to said patient per minute. It is further to be understood, that the patient receives said oxygen flow as supplemental oxygen, through a mask, through a nasal tube or in a similar manner.

It is to be understood that the calculated relationship and projection between the oxygen level of the patient and the arterial oxygenation value of the patient are possible by applying one or more of the mathematical models as required by one, or more, of the below conditions, or model assumptions, C1-C3; and that by applying one of said models, it is clear that the oxygen level and the arterial oxygenation value of the patient are related and thus, it is possible to project an expected arterial oxygen value of a patient, based on an oxygen level of said patient.

Even further, studies indicate that a percentage of patients are treated with long-term oxygen therapy, which are not in need of said treatment, but due to a lack of proper oxygen flow adjustments are diagnosed as suitable for said treatment. This patient group could be reduced by the improved decision support of the present invention and a higher resolution, hence more increments of adjustment, in the oxygen adjustments.

In the context of the present invention, it is to be understood that the term 'calculating' is to be understood in a broad manner, i.e. as including—but not limited to—transforming from into one number into another number, using for example a computer-implemented data processing system.

In the context of the present invention, an adjustment of oxygen flow is also referred to as oxygen titration, and in the context of the present invention, the two terms are interchangeable.

In the context of the present invention, a baseline is to be understood as a starting point, based on a set of observations such as blood gas values and arterial oxygenation values.

In the context of the present invention, adjustment of oxygen flow is to be understood as either increasing or reducing the flow, typically measured in litres of oxygen per minute, based on the specific medical need of a patient.

In the context of the present invention, it is to be understood by a person skilled in physiology that the arterial and venous blood are closely interconnected, the arterial blood being oxygenated from in lungs and conveyed to the capillaries, where the oxygen is used in the metabolism, and subsequently conveyed back to the lungs. Depending on the context, there may accordingly be a gradual transition from arterial blood to capillary blood, and further from capillary blood to venous blood.

In the context of the present invention, the mathematical model for calculating a relationship between an oxygen level (pO2) of the patient and the arterial oxygenation value of the patient may be based on one, or more, of the following conditions (C1, C2 and/or C3), or model assumptions:

C1 The respiratory quotient ($RQ=VCO_2/VO_2RQ$) may be approximated by measurement of inspiratory and expiratory gases taken at the mouth, through the measurement of inspiratory oxygen ($FiO_2$) and carbon dioxide ($FiCO_2$) fraction and either end tidal fractions of oxygen ($Fe'O_2$) and carbon dioxide ($Fe'CO_2$) or mixed expired fractions of oxygen ($FeO_2$) and carbon dioxide ($FeCO_2$), preferably using the equations:

$$RQ = \frac{Fe'CO_2 - FiCO_2}{FiO_2 - Fe'O_2} \text{ or } RQ = \frac{FeCO_2 - FiCO_2}{FiO_2 - FeO_2},$$

C2 Approximation of RQ by the above assumption C1 may often give values which can vary substantially. However, the true value of RQ at the tissues can only vary between 0.7-1.0, being 0.7 in aerobic metabolism of fat and 1.0 in aerobic metabolism of carbohydrate, and/or C3 A mathematical model of blood acid/base and oxygenation status can be used to perform a simulation, where $O_2$ is added and $CO_2$ removed from the venous blood in a ratio determined by a constant respiratory quotient (RQ) set to be within the physiologically possible range 0.7-1.0 from the above condition C2. This simulation may then be performed until the simulated oxygen saturation is equal to that estimated or measured in condition C2, i.e. that in arterial blood.

See also WO 2004/010861 (to OBI Medical Aps, Denmark), which is hereby incorporated by reference in its entirety, the related scientific article "*A method for calculation of arterial acid-base and blood gas status from measurements in the peripheral venous blood*" by Rees et al. in *Computer methods and programs in biomedicine* 81 (2006) pages 18-25, which is also hereby incorporated by reference in its entirety, and the related article *"Mathematical model-ing of the acid-base chemistry and oxygenation of blood: a mass balance mass action approach including plasma and red blood cells"* by Rees et al. in the European journal of applied physiology 108 (2010) pages 483-494, which is also hereby incorporated by reference in its entirety, for more details of a specific model, but other models, or variants thereof, may be applied within the context and principle of the present invention as the skilled person will readily understand.

In the context of the present invention, it is to be under-stood that providing, measuring, and/or estimating blood values from a blood sample does not necessarily include the specific step of taking or extracting a blood sample from a patient, thus measurements results may be obtained, trans-ferred, communicated etc. from another entity or person, e.g. a nurse, having performed a blood measurement or extrac-tion.

In the context of the present invention, approximation is to be understood as calculating or deriving a numerical quantity, through a mathematical method, that is close in value to but not the same as a true quantity. It is further to be understood, that in the context of the present invention, an approximation may be a sufficient method of assessing a quantity in order to accomplish a desired goal, such as assessing an oxygen level based on an approximation.

In the context of the present invention, it is to be under-stood that when receiving a result of the invention may be part of a computer-implemented decision support system (DSS).

In the context of the present invention, the following definitions and abbreviations will be used:

| Abbreviation | Meaning |
|---|---|
| BGA | Blood Gas Analyser - instrument to measure acid-base and blood gas status in blood |
| ABG | Arterial Blood Gas and acid-base |
| VBG | Venous Blood Gas and acid-base |
| PVBG | Peripheral Venous Blood Gas and acid-base |
| CVBG | Central Venous Blood Gas and acid-base |
| CBG | Capillary Blood Gas and acid-base |
| $ABG_M$ | Arterial blood gas values, measured by a blood gas analyser or a similar instrument or method. |
| $VBG_M$ | Venous (or capillary) blood gas values, measured by a blood gas analyser or a similar instrument or method. |
| v-TAC ™ | The v-TAC ™ software, based on the patented method for mathematical arterialisation of venous blood, cf. WO 2004/010861 (to OBI Medical Aps, Denmark), which is hereby incorporated by reference in its entirety. |
| VTAC | Any mathematical algorithm, equation, formula, model, computer program or mechanism, such as but not limited to the v-TAC ™ software, for calculation of $ABG_P$ values from blood, such as but not limited to venous or capillary blood |
| SpO2 | Arterial saturation level measured by pulse oximetry |
| SD | Statistical Deviation (statistic term) |

Thus, in general the subscript 'A' means arterial, the subscript 'V' means venous, the subscript 'M' means mea-sured, the subscript 'E' means estimated, the subscript 'P' means predicated etc. In some of the Figures and/or descrip-tion, the subscript may not be written as a subscript for practical reasons, e.g. 'SO2V', but it will be understood by the skilled person what the technical meaning is.

In an advantageous embodiment of the invention, the blood gas values are derived from a capillary blood sample and wherein the baseline and projection is corrected for an insufficiently arterialized capillary blood sample so as to increase the accuracy of the baseline for the projection and thus increase the accuracy of the suggested target arterial oxygenation value that the health care person should attempt to reach in order to reach the correct oxygen level in the patient.

In the context of the present invention, insufficiently arterialized capillary blood is to be understood as a capillary blood sample wherein more than 1-3% of the blood drawn from the patient, such as from a finger or ear flip, is from venous blood.

In a preferred embodiment of the invention, the arterial oxygenation value is a measured peripheral arterial oxygen saturation value, preferably by pulse oximetry which is non-invasive and thus a minimal inconvenience to a patient.

In another embodiment of the invention, the arterial oxygenation may be provided by other means of measuring said value, invasively or otherwise.

In an embodiment of the invention, the oxygen level in the patient represents a partial pressure of oxygen in the arterial blood of said patient, which is a reliable method of deter-mining if a patient has a sustainable and sufficient supply of oxygen.

In an embodiment of the invention, the medical condition of the patient is a respiratory or cardiac disease, such as chronic obstructive pulmonary disease (COPD), such as interstitial lung disease (ILD), such as Cystic fibrosis (CF), such as pulmonary hypertension, such as patients with neuromuscular or chest wall disorders or such as patients with advanced cardiac failure.

In an embodiment of the invention, the oxygen treatment is a long-term oxygen treatment and the accuracy of the present invention increases the comfort of the patient and reduces the resources spent on unnecessary treatment, such as a "higher than required to sustain steady and sufficient oxygen level" oxygen flow.

In another embodiment of the present invention, the oxygen treatment is an acute treatment of a patient in relation to trauma or a sudden onset of a pathology requiring emergent care, in which the invention is advantageous for a fast and reliable adjustment of the oxygen flow supplied to the patient.

In the context of the present invention, long-term oxygen treatment is to be understood as oxygen treatment for at least 12 hours per day for more than 30 days. It should be noted that a person skilled in the art would know the difference between acute and long-term oxygen treatment.

In an advantageous embodiment of the invention, the titrated oxygen flow to accomplish a desired oxygen level within a patient is accomplished, with no more than two, such as no more than 4, such as no more than 6 or such as no more than 10 blood gas measurements from two, such as from 4, such as from 6 or such as from 10 blood samples, wherein a first blood sample is a baseline sample and another blood sample is a confirmatory sample so as to:

a) save time and resources spent by health care personnel on acquiring said blood samples, and b) discomfort to the patient due to an excessive number of blood samples drawn from said patient.

In an embodiment of the invention, the relationship rep-resents an oxygen dissociation curve (ODC) for a specific blood sample as the oxygen dissociation curve is known and recognized by health care personnel as stable due to, under normal circumstances, small or marginal shifts in pH, 2.3-DPG, fMetHb and fCOHb, and thus enables a health care person to understand what the present invention is suggest-ing and why oxygen, if needed, should be supplied to the patient.

In another embodiment of the invention, the projection of the baseline is an approximation of the oxygen dissociation curve based on a specific blood sample from a patient as the oxygen dissociation curve, under most circumstances are stable and predictable, so that the projection will be stable and reliable.

In a preferred embodiment of the invention, the patient specific projection of the oxygen dissociation curve and/or the target oxygen level and/or target arterial oxygenation value is printed or displayed on a display, such as on a computer monitor, a portable tablet, or a mobile phone screen.

In an advantageous embodiment of the invention, a value of arterial oxygenation is provided to the health care person before and/or after an adjustment of the oxygen flow so as to ensure that the health care person is continuously aware of the patients oxygen level thus increasing the accuracy of the adjustments performed to the oxygen flow to the patient.

In a preferred embodiment of the invention, the decision support further comprises:

Step 1:—providing a desired target oxygen level to the decision support, wherein the decision support calculates a target arterial oxygenation value based on the provided blood gas values and a first arterial oxygenation value, the decision support suggests an oxygen flow adjustment and a wait time until a second arterial oxygenation value is to be provided to the decision support so as to further assist the health care person when adjusting the oxygen flow to the patient and increase the accuracy of the decided oxygen flow, reducing time spent on adjusting said oxygen flow and reducing discomfort to the patient.

In a further preferred embodiment, the decision support further comprises the steps of, after Step 1, as mentioned above:

Step 2:—providing a present arterial oxygenation value of the patient after the wait time, wherein the decision support, if the target arterial oxygenation value is not reached, suggests an oxygen flow adjustment and a wait time until a next arterial oxygenation value is to be provided to the decision support, Step 3:—repeating Step 2 until the target arterial oxygenation value is reached so as to further assist the health care person when adjusting the oxygen flow to the patient and increase the accuracy of the decided oxygen flow, reducing time spent on adjusting said oxygen flow and reducing discomfort to the patient.

In an advantageous embodiment of the invention, the decision support suggests a final oxygen flow to reach the patients target oxygen level based on a first blood gas value and an optional first arterial oxygenation value so as to even further assist the health care person when adjusting the oxygen flow to the patient and reducing time spent on adjusting said oxygen flow and thus reducing discomfort to the patient.

In some embodiments, the mathematical model may apply that the true value of respiratory quotient (RQ) at the tissues can only vary between 0.7-1.0, being 0.7 in aerobic metabolism of fat and 1.0 in aerobic metabolism of carbohydrate. Additionally, or alternatively, in other embodiments, the mathematical model may apply that oxygen O2 is added and carbon dioxide CO2 removed from the venous blood in a ratio determined by a constant respiratory quotient (RQ), set to be within the physiologically possible range 0.7-1.0, and performing a simulation until the simulated oxygen saturation is equal, or substantially equal, to that estimated or measured in arterial blood.

In an embodiment of the invention, the relationship between an oxygen level of the patient and the arterial oxygenation value of the patient is calculated by applying a mathematical model to the said measured arterial oxygenation value and said measured blood gas values and said projection of the oxygen level from said baseline, wherein a condition of the mathematical model can be expressed as:

$$RQ = \frac{Fe'CO_2 - FiCO_2}{FiO_2 - Fe'O_2}$$

wherein $Fe'O_2$ and $Fe'CO_2$ are end tidal fractions of oxygen and carbon dioxide respectively.

In another embodiment of the invention, the relationship between an oxygen level of the patient and the arterial oxygenation value of the patient is calculated by applying a mathematical model to the said measured arterial oxygenation value and said measured blood gas values and said projection of the oxygen level from said baseline, wherein a condition of the mathematical model can be expressed as:

$$RQ = \frac{FeCO_2 - FiCO_2}{FiO_2 - FeO_2}$$

wherein $FeO_2$ and $FeCO_2$ are mixed expired fractions of oxygen and carbon dioxide respectively.

In a second aspect, the invention relates to a data processing system for providing decision support (DS), said data processing system comprising:

means for receiving blood gas values in a blood sample from a patient to determine a baseline, means for receiving an arterial oxygenation value of the patient, if said blood gas values are not derived from an arterial blood sample, means for calculating a relationship between an oxygen level of the patient and the arterial oxygenation value of the patient by applying a mathematical model to the measured arterial oxygenation value and measured blood gas values and projection of the oxygen level from said baseline, means for calculating a target arterial oxygenation value representing a desired target oxygen level of the patient based on said calculated relationship and projection between the oxygen level of the patient and the arterial oxygenation value of the patient, means for providing decision support for adjusting the oxygen flow from the supplemental oxygen device to the patient based on the measured arterial oxygen value of the patient, until the target arterial oxygenation level is reached, and optional means for measuring the blood gas value in a blood sample from the patient to confirm the desired target oxygen level of the patient is reached, wherein the data processing system provides decision support in relation to a patient receiving oxygen treatment, said patient having a medical condition requiring a supplemental oxygen device providing an oxygen flow, wherein the decision support assists a health care person in adjusting the oxygen flow from said supplemental oxygen device to the patient.

In a preferred embodiment of the invention, the data processing system according to the second aspect of the invention, further comprises means for adjusting the oxygen flow based on a provided value from a patients arterial oxygenation so as to automatically and with high precision, adjust the oxygen flow to the patient in a fast and reliable manner.

In a third aspect, the invention relates to a computer program product enabling a computer system, preferably a portable computer system, to carry out the operations of the system of the second aspect of the invention when down- or uploaded into the computer system.

This aspect of the invention is particularly, but not exclusively, advantageous in that the present invention may be accomplished by a computer program product enabling a computer system to carry out the operations, or steps, of the computer implemented method of the first aspect of the invention when down- or uploaded into the computer, or computer system. Such a computer program product may be provided on any kind of computer readable medium, or through a network.

In a fourth aspect, the invention relates to a medical device suitable for oxygen treatment of a patient, said patient having a medical condition requiring a supplemental oxygen flow, the medical device comprising:

an oxygen device for supplying oxygen flow from a source to said patient, a blood gas measurement device for measuring blood gas values, from a blood sample from said patient, a processing unit for calculating a target arterial oxygenation value representing a desired target oxygen level (target_pO2) of the patient patient based on a calculated relationship and projection between an oxygen level of the patient and an arterial oxygenation value of the patient, and in which an operator provides the medical device with a measured arterial oxygen level of the patient, and the medical device automatically adjusts the oxygen flow from the oxygen device to the patient, based on the measured arterial oxygen value of the patient, until the target arterial oxygenation level is reached.

In an advantageous embodiment of the invention, the blood gas measurement device measures blood gas values based on a venous blood sample.

I another advantageous embodiment of the invention, the arterial oxygenation value is a measured peripheral arterial oxygen saturation value, preferably by pulse oximetry.

In another advantageous embodiment of the invention, the blood gas measurement device measures blood gas values based on a capillary blood sample.

In a fifth aspect, the invention relates to the use of a medical device, for the treatment of patients suffering from a respiratory or cardiac disease, according to the fourth aspect of the invention.

In a sixth aspect, the invention relates to a method of treating cardiac or pulmonary diseases based on a calculated arterial oxygenation level and a supplemental oxygen flow level, according to the invention as disclosed in the first aspect.

The individual aspects of the present invention may each be combined with any of the other aspects. These and other aspects of the invention will be apparent from the following description with reference to the described embodiments.

BRIEF DESCRIPTION OF THE FIGURES

The computer implemented method for providing decision support in relation to a patient receiving oxygen treatment, according to the invention will now be described in more detail with regard to the accompanying figures. The figures show one way of implementing the present invention and is not to be construed as being limiting to other possible embodiments falling within the scope of the attached claim set.

FIG. 7 is a table simulating oxygen adjustment procedures comparing time spent with various methods.

FIG. 9 shows a reduction in a patient receiving oxygen.

DETAILED DESCRIPTION OF AN EMBODIMENT

Figure 1:
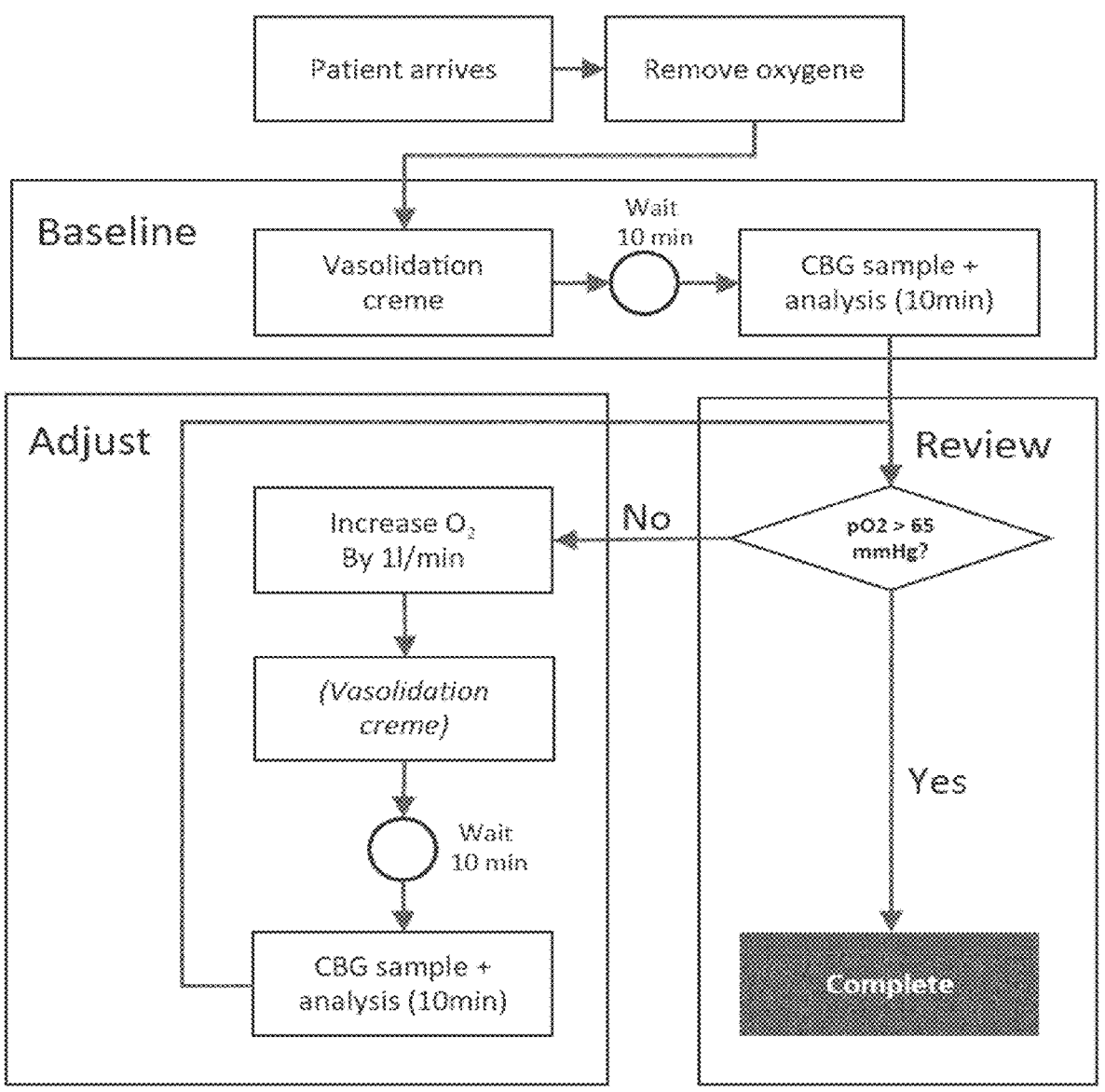
FIG. 1 is a schematic system-chart illustrating current oxygen-adjustment procedures, representing prior art.

FIG. 1 is a prior art oxygen adjustment procedure based on current guidelines, in which a patient arrives for an oxygen adjustment, the supplementary oxygen is removed from the patient, a vasodilation cream is applied to the patient, such as to the patients finger, a ten minute wait time is spent waiting for the vasodilation cream to take effect so as to increase the amount of arterial blood in the finger, obtaining a capillary blood sample from the finger and analyse said sample, review the sample and determine whether the partial pressure of oxygen in the arterial blood, PO2, of the patient are below a target, such as 65 mmHg. If the PO2 is lower than the target, supplementary oxygen flow to the patient is increased by a volume, such as 1 litre/minute and the procedure is repeated, starting with the vasodilation cream and 10 minute wait time, until the oxygen flow is adjusted so as to reach the set target of the PO2.

Figure 2:
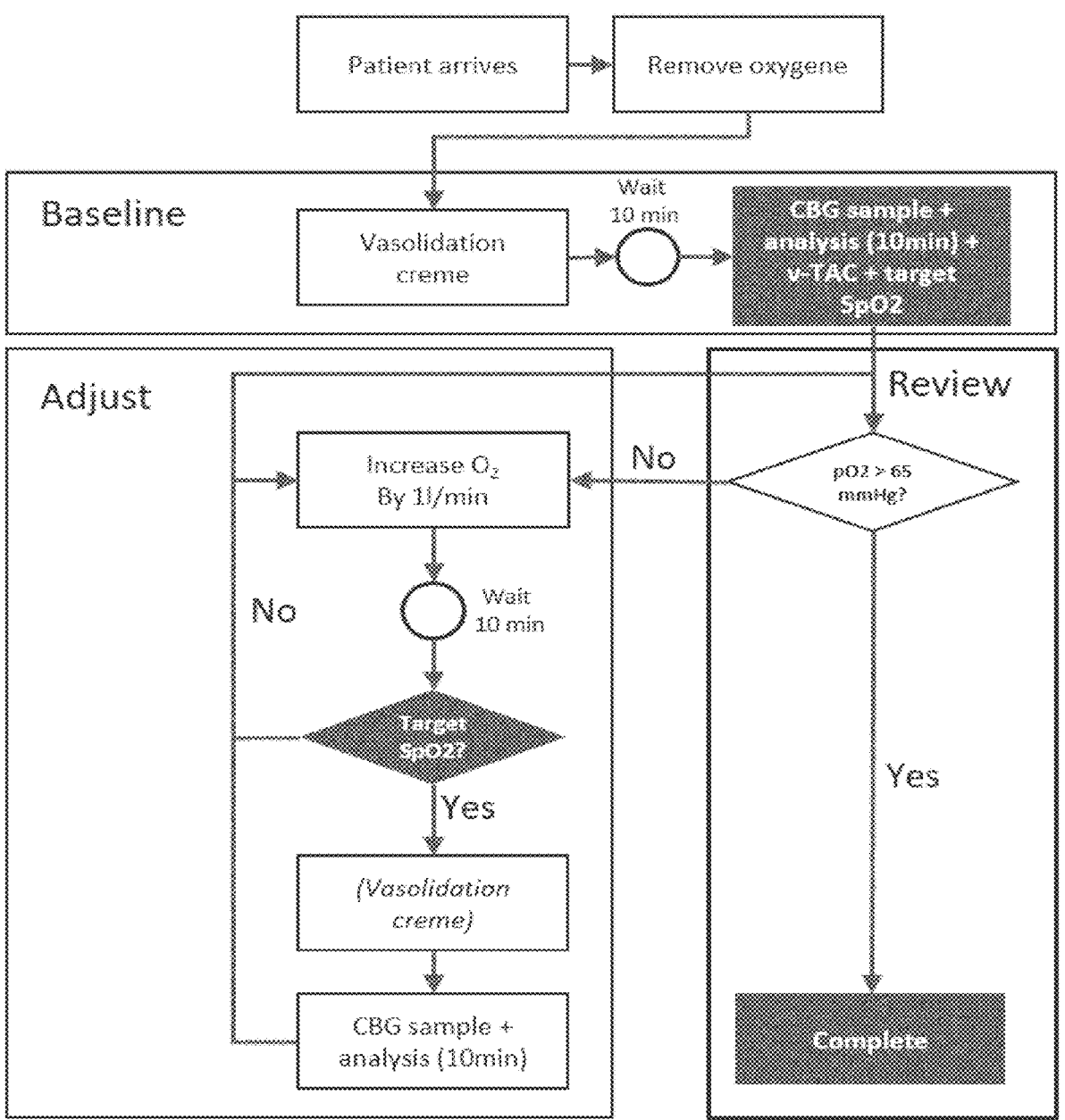
FIG. 2 is a schematic system-chart illustrating a novel oxygen adjustment procedure.

FIG. 2 is a schematic system-chart illustrating a novel oxygen adjustment procedure, in which a baseline is calculated and utilized to extrapolate a peripheral oxygen saturation measurement, SpO2, calculate a target SpO2 corresponding to a desired target PO2 value and use the extrapolated value to adjust the oxygen flow to a patient. The patient arrives for an oxygen adjustment, the supplementary oxygen is removed from the patient, a vasodilation cream is applied to the patient, such as to the patients finger, a ten minute wait time is spent waiting for the vasodilation cream to take effect so as to increase the amount of arterial blood in the finger, obtaining a capillary blood sample from the finger and analyse said sample, obtain a pulse oximetry measurement, review the samples and determine whether the partial pressure of oxygen in the arterial blood, PO2, of the patient are below a target, such as 65 mmHg. If the PO2 is lower than the target, supplementary oxygen flow to the patient is increased by a volume, such as 1 litre/minute and the calculated SpO2 value is used to measure the effect of the increase in oxygen flow. If the SpO2 value is lower than the target SpO2 value after the patient has reached steady state, such as after ten minutes, the oxygen flow is increased by e.g. 1 litre/min and a new SpO2 value is measured to monitor the effect of the increase in oxygen flow. When the target SpO2 value is reached, vasodilation cream is applied and after a wait time, a new capillary blood sample is analysed to ensure that the correct partial pressure of oxygen in the arterial blood is reached, finalizing the oxygen adjustment procedure.

Figure 3:
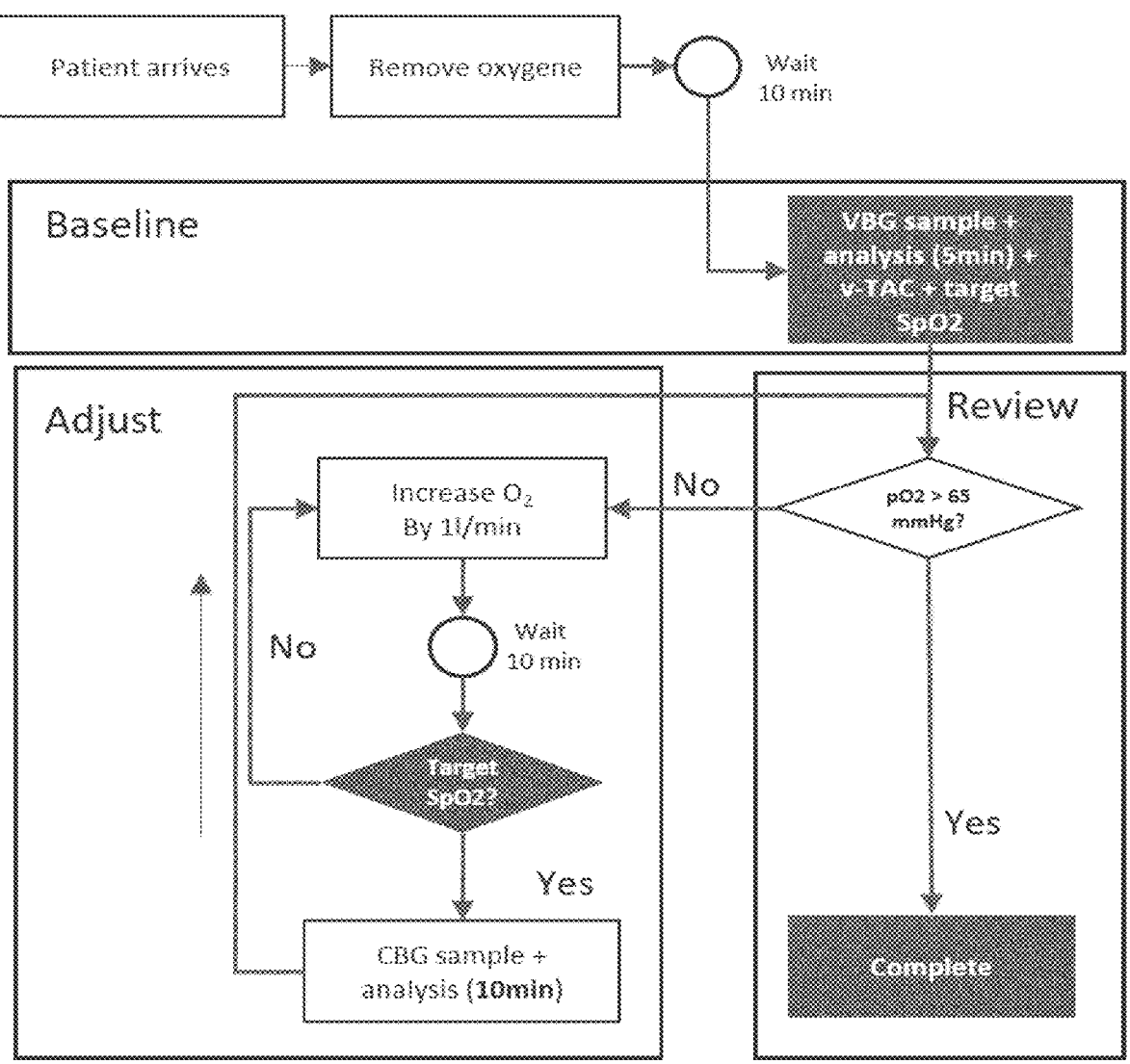
FIG. 3 is a schematic system-chart illustrating a second novel oxygen adjustment procedure.

FIG. 3 is a schematic system-chart illustrating a second novel oxygen adjustment procedure, in which a baseline is calculated and utilized to extrapolate a peripheral oxygen saturation measurement, SpO2, calculate a target SpO2 corresponding to a desired target PO2 value and use the extrapolated value to adjust the oxygen flow to a patient. The patient arrives for an oxygen adjustment, the supplementary oxygen is removed from the patient, a venous blood sample is provided, a pulse oximetry measurement is provided, the samples are analysed an reviewed and it is determined whether the partial pressure of oxygen in the arterial blood, PO2, of the patient are below a target, such as 65 mmHg. If the PO2 is lower than the target, supplementary oxygen flow to the patient is increased by a volume, such as 1 litre/minute and the calculated SpO2 value is used to measure the effect of the increase in oxygen flow. If the SpO2 value is lower than the target SpO2 value after the patient has reached steady state, such as after ten minutes, the oxygen flow is increased by e.g. 1 litre/min and a new SpO2 value is measured to monitor the effect of the increase in oxygen flow. When the target SpO2 value is reached a capillary blood sample is analysed to ensure that the correct partial pressure of oxygen in the arterial blood is reached, finalizing the oxygen adjustment procedure.

Figure 4:
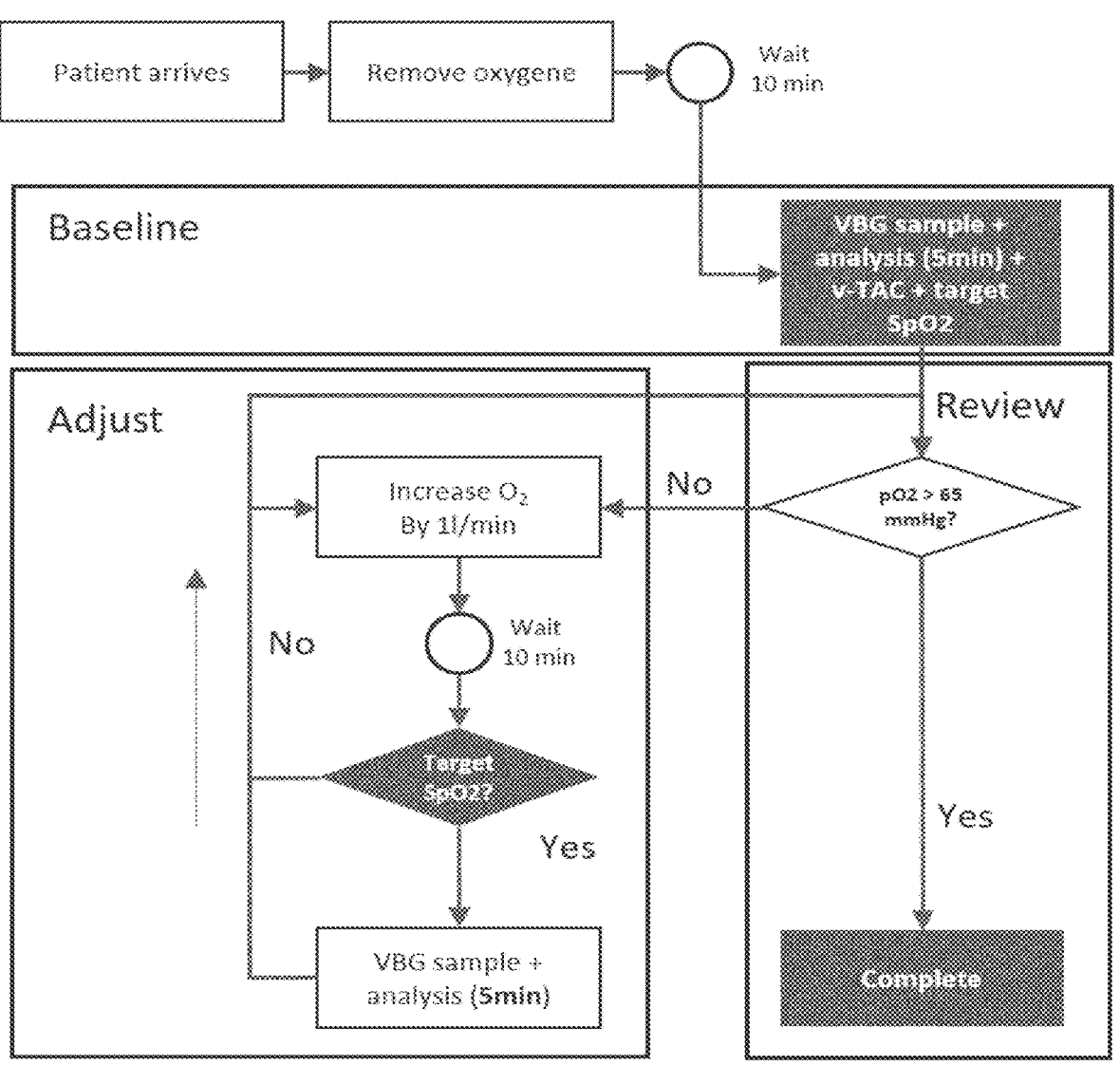
FIG. 4 is a schematic system-chart illustrating a third oxygen adjustment procedure.

FIG. 4 is a schematic system-chart illustrating a third novel oxygen adjustment procedure, in which a baseline is calculated and utilized to extrapolate a peripheral oxygen saturation measurement, SpO2, calculate a target SpO2 corresponding to a desired target PO2 value and use the extrapolated value to adjust the oxygen flow to a patient. The patient arrives for an oxygen adjustment, the supplementary oxygen is removed from the patient, a venous blood sample is provided, a pulse oximetry measurement is provided, the samples are analysed an reviewed and it is determined whether the partial pressure of oxygen in the arterial blood, PO2, of the patient are below a target, such as 65 mmHg. If the PO2 is lower than the target, supplementary oxygen flow to the patient is increased by a volume, such as 1 litre/minute and the calculated SpO2 value is used to measure the effect of the increase in oxygen flow. If the SpO2 value is lower than the target SpO2 value after the patient has reached steady state, such as after ten minutes, the oxygen flow is increased by e.g. 1 litre/min and a new SpO2 value is measured to monitor the effect of the increase in oxygen flow. When the target SpO2 value is reached a venous blood sample is analysed to ensure that the correct partial pressure of oxygen in the arterial blood is reached, finalizing the oxygen adjustment procedure.

Figure 5:
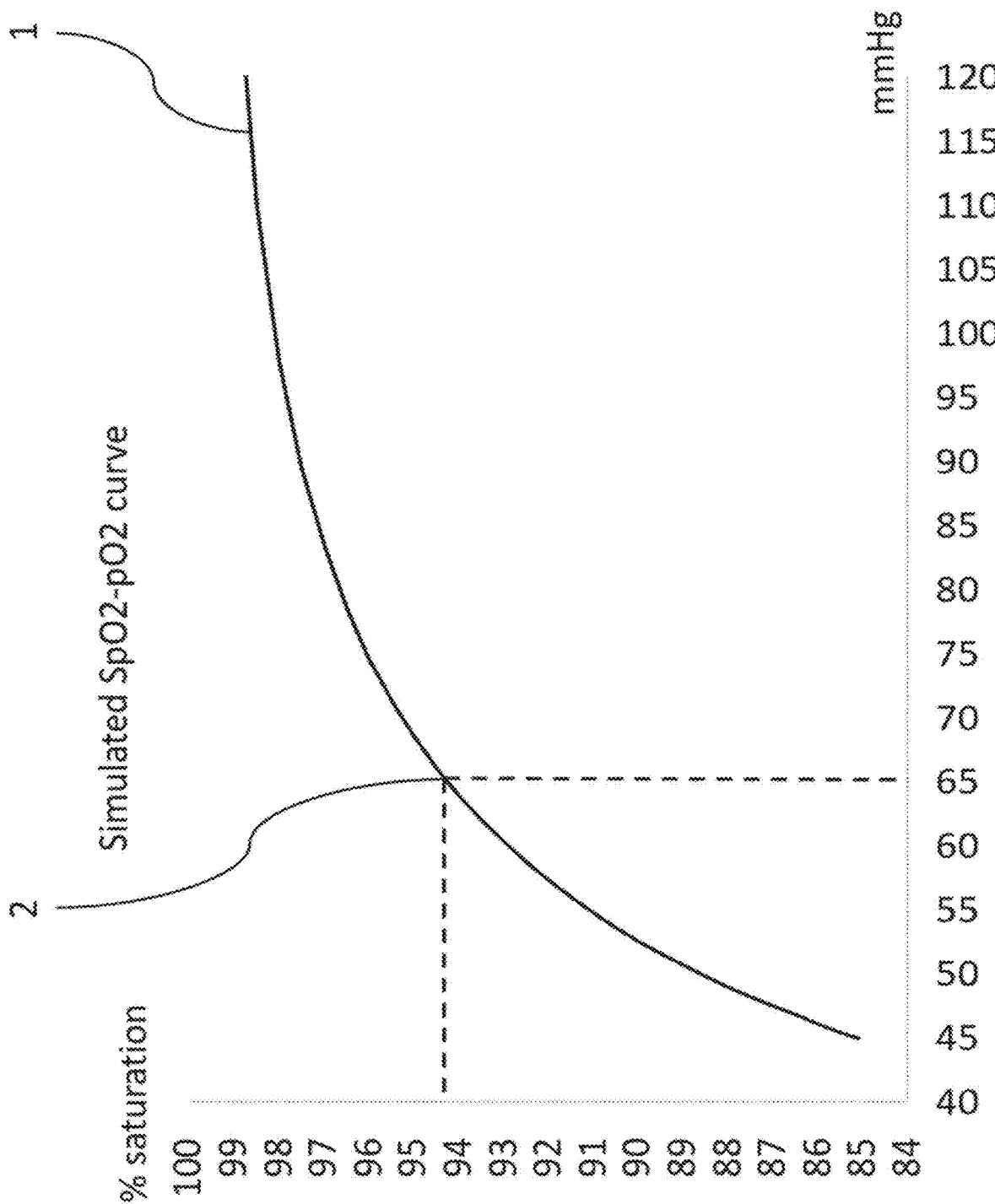
FIG. 5 is a graph illustrating an oxygen dissociation curve.

FIG. 5 is a graph illustrating a simulated oxygen dissociation curve 1, wherein the intersection 2 of the two dotted lines indicates an example of a desired target value, for a partial pressure of oxygen in the arterial blood. The x-axis represents the partial pressure of oxygen in the arterial blood, measured as mmHg and the y-axis represents the oxygen saturation percentage of peripheral blood. In the present example a target value of partial pressure of oxygen in the arterial blood is set at 65 mmHg on the x-axis and when reading the corresponding percentage of saturation of peripheral blood, by projecting the intersected point on the curve 1, the value of y is 94%.

Figure 6:
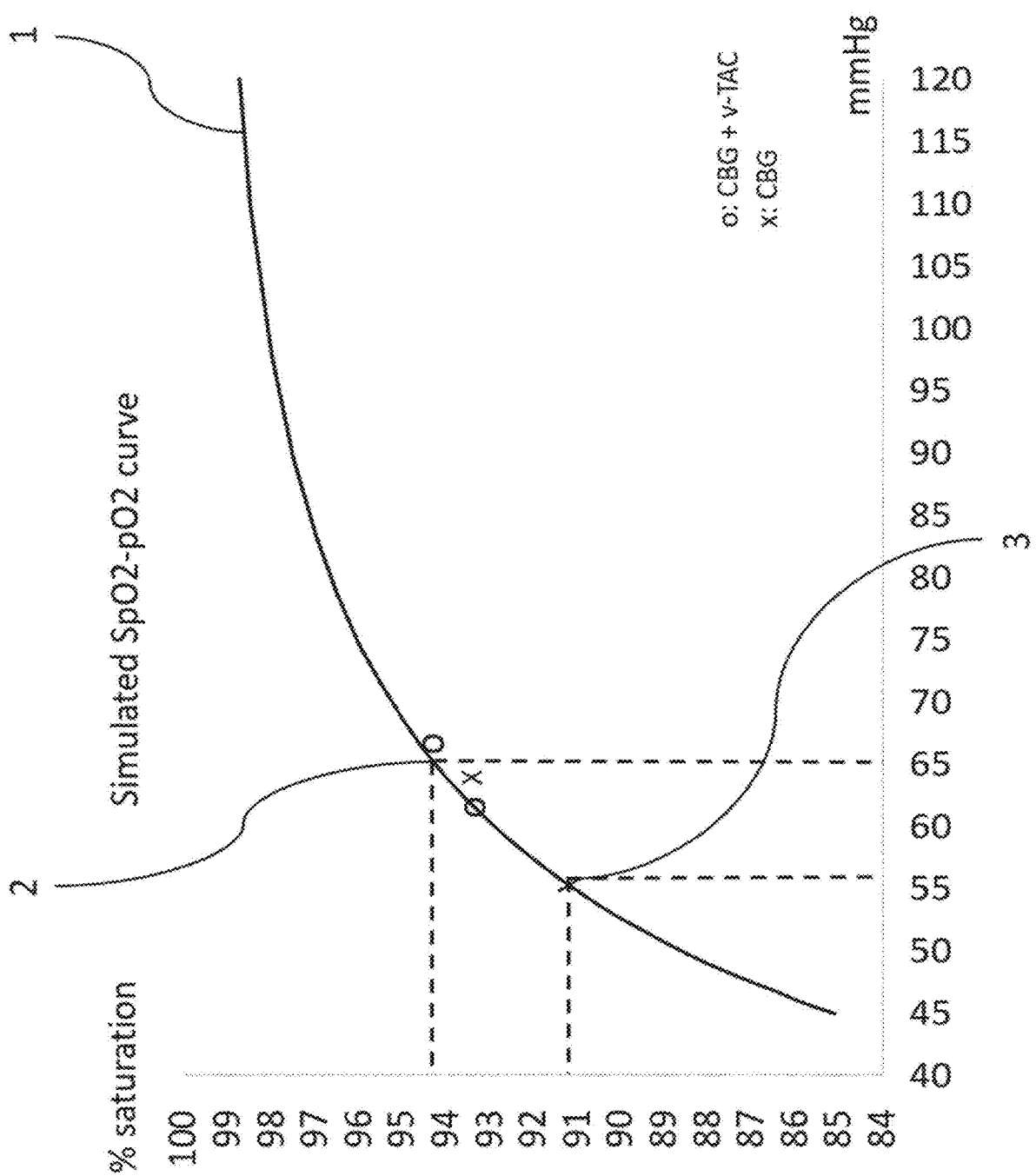
FIG. 6 is a graph illustrating another oxygen dissociation curve.

FIG. 6 is a graph illustrating a simulated oxygen dissociation curve 1, wherein the intersection 2 of the first two dotted lines indicates an example of a desired target value, for a partial pressure of oxygen in the arterial blood. The x-axis represents the partial pressure of oxygen in the arterial blood, measured as mmHg and the y-axis represents the oxygen saturation percentage of peripheral blood. In the present example a target value of partial pressure of oxygen in the arterial blood is set at 65 mmHg on the x-axis and when reading the corresponding percentage of saturation of peripheral blood, by projecting the intersected point on the curve 1, the value of y is 94%. The intersection 3 of the second set of dotted lines represents a measured baseline value of a blood sample and a pulse oximetry of a patient. The baseline can be used to extrapolate or project an oxygen dissociation curve intersecting with said baseline so as to enable the invention to calculate a target value of % saturation of e.g. a pulse oximetry readout based on a desired target value of mmHg of partial pressure of oxygen in the arterial blood. In the figure, 'x' on the curve illustrates a measured level of partial pressure of oxygen in the arterial blood based on a capillary blood sample and 'o' represents a calculated value of oxygen in the arterial blood from a calculation based on the baseline value and a pulse oximetry readout.

FIG. 7 is a table simulating oxygen adjustment procedures comparing time spent with various methods. CBG for all demonstrates that patients using an existing method averages 52 minutes in an oxygen treatment procedure. CBG with target reduces the procedure by 6 minutes to 46 minutes, VBG+v-TAC for baseline combined with CBG+v-TAC for final reduces the procedure by 11 minutes to 41 minutes and VBG+v-TAC for baseline and VBG+v-TAC for final reduces the procedure by 16 minutes to 36 minutes.

Figure 8:
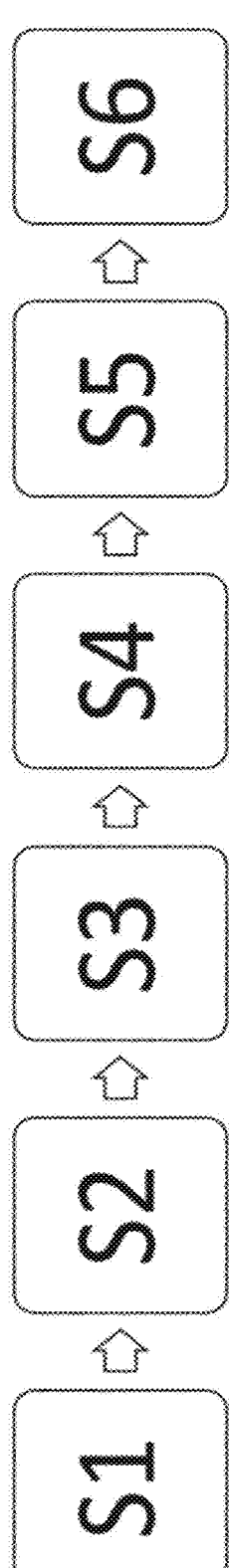
FIG. 8 is a schematic system-chart representing an outline of the operations of the computer program product according to the invention.

FIG. 8 is a schematic flow-chart representing an out-line of the operations of the computer implemented method according to the invention, the method comprising:

S1—providing blood gas values in a blood sample from the patient to determine a baseline, S2—providing an arterial oxygenation value of the patient, if said blood gas values are not derived from an arterial blood sample, S3—calculating a relationship between an oxygen level of the patient and the arterial oxygenation value of the patient by applying a mathematical model to the measured arterial oxygenation value and measured blood gas values and projection of the oxygen level from said baseline, S4—calculating a target arterial oxygenation value representing a desired target oxygen level, target_pO2, of the patient based on said calculated relationship and projection between the oxygen level of the patient and the arterial oxygenation value of the patient, S5—providing decision support for adjusting the oxygen flow from the supplemental oxygen device to the patient based on the measured arterial oxygen value of the patient, until the target arterial oxygenation level is reached, and S6—optionally providing the blood gas value in a blood sample from the patient to confirm the desired target oxygen level of the patient is reached The inventors have performed an analysis of 10 patients getting an LTOT oxygen titration (oxygen adjustment). Table 1 shows an average number of samples for a procedure being 2.6 per patient. The patient process time is reduced by 11% (average time comparison between Table 1 and Table 2), and sample time by 23%. 10% (n=1) patient receiving oxygen would not have received oxygen, further demonstrating the importance of the invention as shown in FIG. 9.

TABLE 1

| Oxygene/ samples | Patients (N = 10)/ Samples | Time used (min) | Total time (min) |
|---|---|---|---|
| 0 l/min/1 | 0 pts/0 smpl. | 20 | 0 |
| 1 l/min/2 | 6 pts/12 smpl. | 40 | 240 |
| 2 l/min/3 | 2 pts/6 smpl. | 60 | 120 |
| 3 l/min/4 | 2 pts/8 smpl. | 80 | 160 |
| 4 l/min/5 | 0 pts/0 smpl. | 100 | 0 |
| Average | 2.6 samples | | 52 min |

TABLE 1

| Oxygene | Patients (N = 10) | Total time (min) | Sample time (min) |
|---|---|---|---|
| 0 l/min/1 | 0/0 | 20 | 0 |
| 1 l/min/2 | 6 | 40 | 240 |
| 2 l/min/2 | 2 | 50 | 100 |
| 3 l/min/2 | 2 | 60 | 120 |
| 4 l/min/2 | 0 | 70 | 0 |
| Average | | | 46 min |

The invention can be implemented by means of hardware, software, firmware or any combination of these. The invention or some of the features thereof can also be implemented as software running on one or more data processors and/or digital signal processors.

The individual elements of an embodiment of the invention may be physically, functionally and logically implemented in any suitable way such as in a single unit, in a plurality of units or as part of separate functional units. The invention may be implemented in a single unit, or be both physically and functionally distributed between different units and processors.

Although the present invention has been described in connection with the specified embodiments, it should not be construed as being in any way limited to the presented examples. The scope of the present invention is to be interpreted in the light of the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures and/or formulas shall also not be construed as limiting the scope of the invention, such as (target_p02), (pO2), (target Sp02), (SpO2) (CBG), (ABG), (VBG) etc. Furthermore, individual features mentioned in different claims, may possibly be advantageously combined, and the mentioning of these features in different claims does not exclude that a combination of features is not possible and advantageous.

The invention claimed is:

1. A computer-implemented oxygen treatment and decision support system for a patient having a medical condition requiring a supplemental oxygen flow, the system comprising:

an oxygen device configured to supply oxygen flow from a source to the patient;

a device configured to provide a measured arterial oxygenation value of the patient;

a blood gas measurement device configured to acquire a baseline blood gas value from at least one of a venous blood sample of the patient or a capillary blood sample of the patient, and a processing unit configured to:

transform the baseline blood gas value into an arterial equivalent by simulating a metabolic oxygen addition to and metabolic carbon dioxide removal from the venous blood sample in a ratio determined by a constant respiratory quotient set that is bounded by a value that corresponds to an aerobic metabolism of fat and a value that corresponds to an aerobic metabolism of carbohydrate;

calculate a target arterial oxygenation value based on an oxygen dissociation curve between the arterial equivalent of the baseline blood gas value level of the patient and the measured arterial oxygenation value; and automatically adjust the oxygen flow from the oxygen device to the patient until the target arterial oxygenation value is reached.

2. The computer-implemented decision support system according to claim 1, in which the blood gas measurement device measures the baseline blood gas value based on a venous blood sample.

3. The computer-implemented decision support system according to claim 1, in which the blood gas measurement device measures the baseline blood gas value based on a capillary blood sample.

4. The computer-implemented decision support system according to claim 1, in which the device configured to provide an arterial oxygenation value comprises a pulse oximeter such that the measured arterial oxygenation value is a measured peripheral arterial oxygen saturation value.

5. The computer-implemented decision support system according to claim 1, wherein the physiologically possible range of the respiratory quotient is between of 0.7 and 1.0.

* * * * *